(12) United States Patent
Stewart et al.

(10) Patent No.: US 11,006,868 B2
(45) Date of Patent: May 18, 2021

(54) SYSTEM AND METHOD FOR INTRAOPERATIVE DETECTION OF CANCER MARGINS USING CONFORMAL FILTERS IN A DUAL POLARIZATION CONFIGURATION

(71) Applicant: CHEMIMAGE TECHNOLOGIES LLC, Pittsburgh, PA (US)

(72) Inventors: Shona Stewart, Pittsburgh, PA (US);
Serena Augustine, Pittsburgh, PA (US);
Jeffrey Cohen, Pittsburgh, PA (US);
Ryan Priore, Wexford, PA (US)

(73) Assignee: CHEMIMAGE TECHNOLOGIES LLC, Pittsburgh, PA (US)

( * ) Notice: Subject to any disclaimer, the term of this patent is extended or adjusted under 35 U.S.C. 154(b) by 138 days.

(21) Appl. No.: 15/813,766

(22) Filed: Nov. 15, 2017

(65) Prior Publication Data

US 2018/0199863 A1 Jul. 19, 2018

Related U.S. Application Data

(62) Division of application No. 14/302,225, filed on Jun. 11, 2014, now Pat. No. 9,844,334.

(Continued)

(51) Int. Cl.
| | |
|---|---|
| *A61B 5/1459* | (2006.01) |
| *H03K 19/173* | (2006.01) |
| *A61B 34/30* | (2016.01) |
| *A61B 5/1473* | (2006.01) |
| *A61B 17/00* | (2006.01) |

(Continued)

(52) U.S. Cl.
CPC .......... *A61B 5/1459* (2013.01); *A61B 5/1473* (2013.01); *A61B 5/4519* (2013.01); *A61B 17/00234* (2013.01); *A61B 34/30* (2016.02); *G01N 21/255* (2013.01); *H03K 19/1735* (2013.01); *A61B 2034/302* (2016.02); *G01J 3/0224* (2013.01); *G01N 2201/06113* (2013.01)

(58) Field of Classification Search
CPC ... A61B 5/0059; A61B 5/0084; A61B 5/1459; A61B 5/4519; A61B 34/30; A61B 5/1473; A61B 17/00234; A61B 2034/302; G01N 21/255; G01N 2201/06113; H03K 19/1735; G01J 3/0224
See application file for complete search history.

(56) References Cited

U.S. PATENT DOCUMENTS

| | | |
|---|---|---|
| 7,990,533 B2 | 8/2011 | Maier et al. |
| 8,167,794 B2 | 5/2012 | Matsumoto et al. |

(Continued)

FOREIGN PATENT DOCUMENTS

WO 2014074569 A1 5/2014

OTHER PUBLICATIONS

Wang et al., Three-Dimensional Imaging of Ureter With Endoscopic Optical Coherence Tomography, Urology (May 2011), 77(5):1254-1258.

*Primary Examiner* — Hien N Nguyen
(74) *Attorney, Agent, or Firm* — Troutman Pepper Hamilton Sanders LLP

(57) ABSTRACT

Devices, systems, and methods for distinguishing tissue types are described herein. Such devices and systems may use dual polarization, conformal filters to acquire image data from target tissues and a processor to create an image in which the contrast between tissues has been enhanced.

16 Claims, 11 Drawing Sheets

Related U.S. Application Data

(60) Provisional application No. 61/833,622, filed on Jun. 11, 2013.

(51) Int. Cl.
*G01N 21/25* (2006.01)
*A61B 5/00* (2006.01)
*G01J 3/02* (2006.01)

(56) References Cited

U.S. PATENT DOCUMENTS

| | | | |
|---|---|---|---|
| 2006/0192965 A1* | 8/2006 | Tromberg | A61B 5/0059 356/432 |
| 2008/0054174 A1* | 3/2008 | Boyle | G01N 27/624 250/286 |
| 2009/0299946 A1* | 12/2009 | Myrick | G01J 3/02 706/52 |
| 2009/0309049 A1 | 12/2009 | Van Dijk et al. | |
| 2010/0309464 A1 | 12/2010 | Treado et al. | |
| 2012/0083678 A1 | 4/2012 | Drauch et al. | |
| 2013/0176568 A1 | 7/2013 | Priore et al. | |
| 2016/0213252 A1 | 7/2016 | Hillman et al. | |

\* cited by examiner

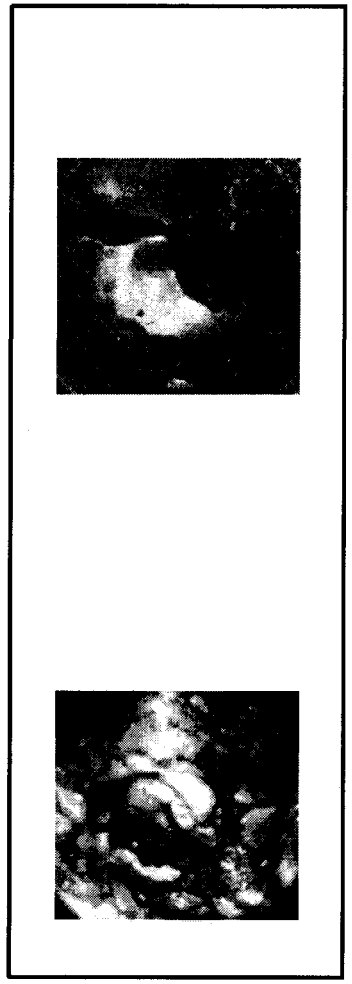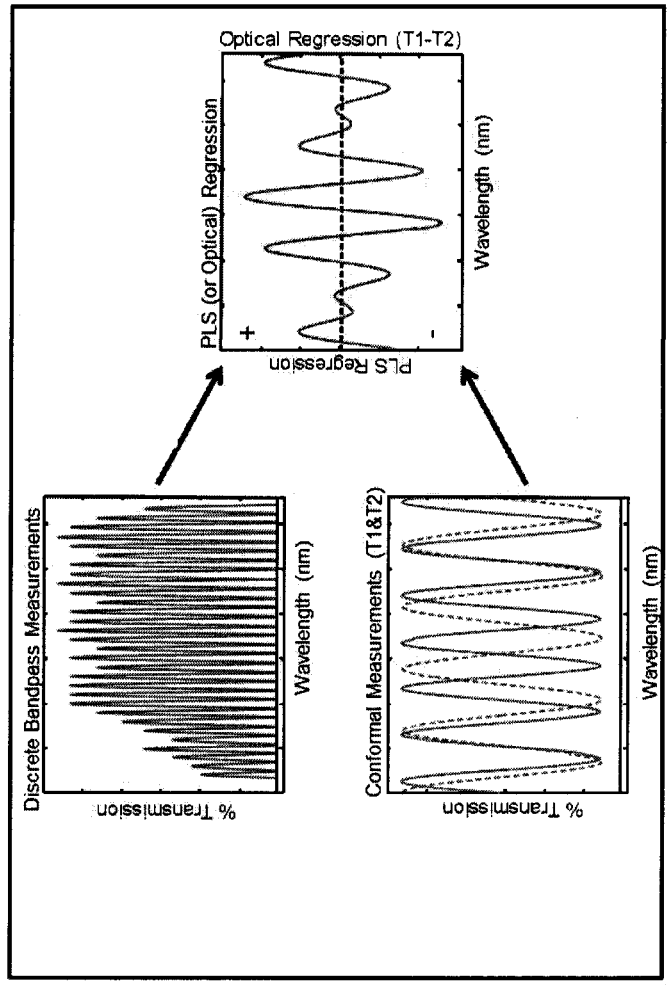
FIG. 6A
FIG. 6B
FIG. 6

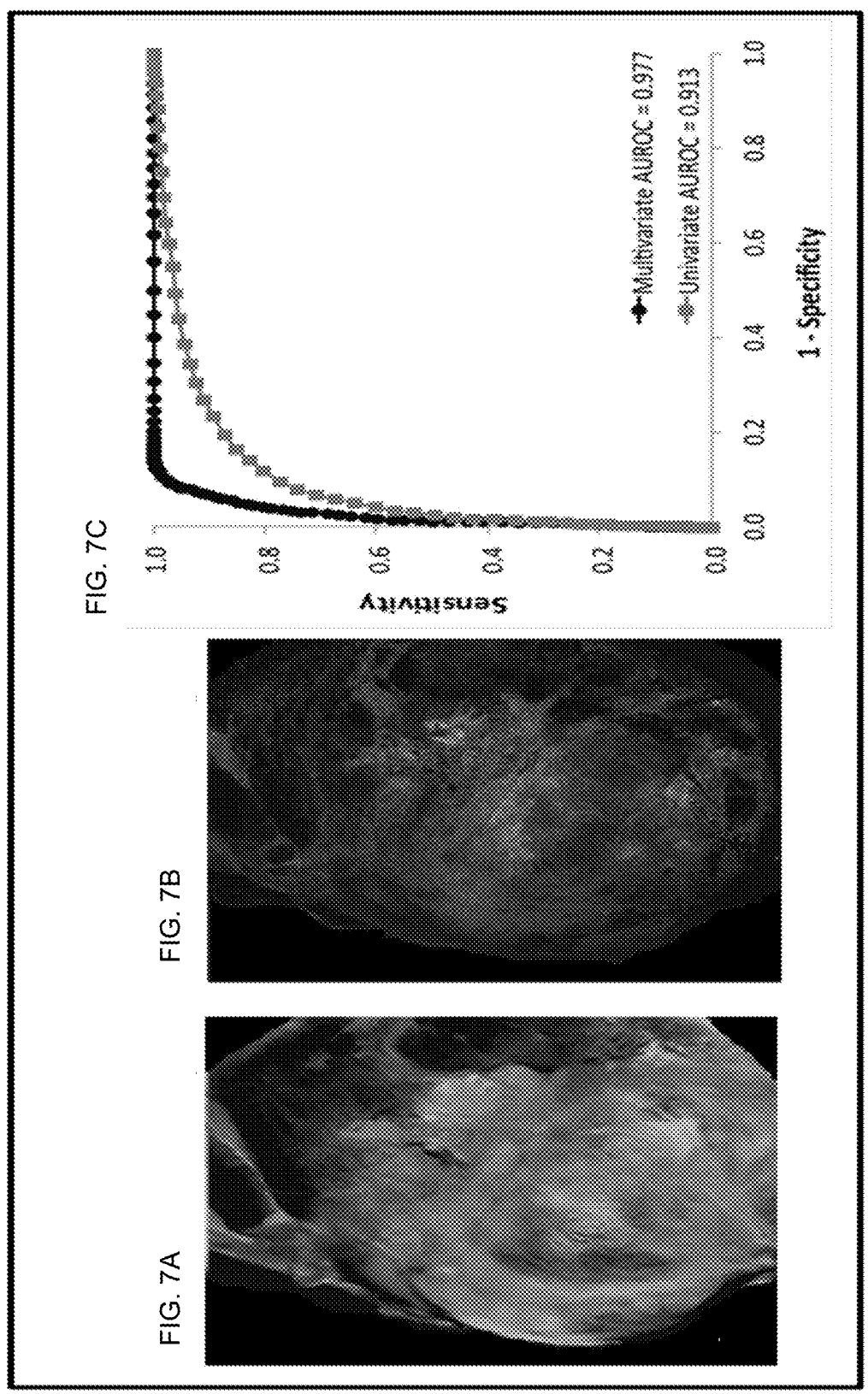

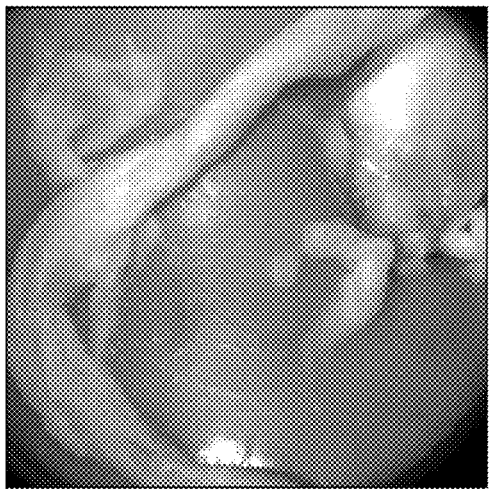
FIG. 8B
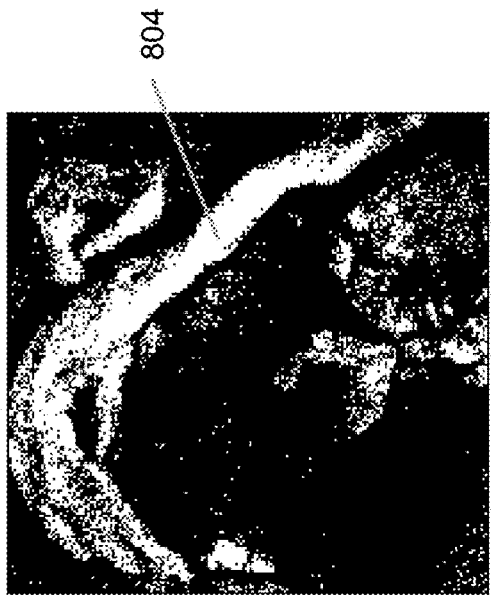
FIG. 8D
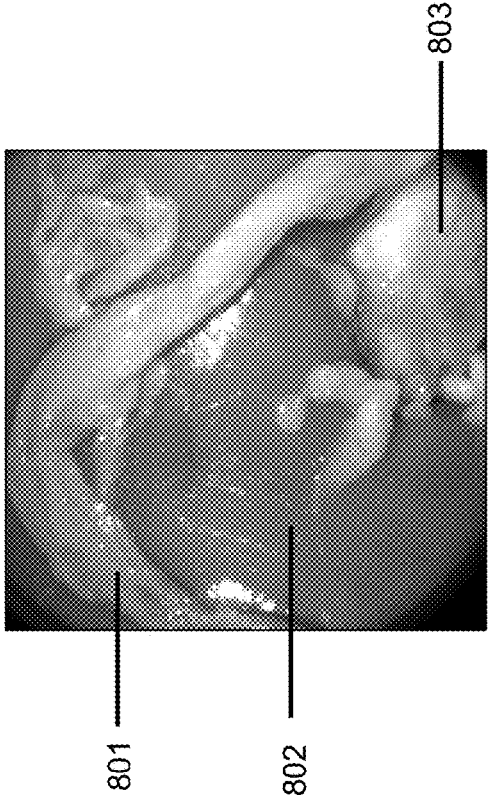
FIG. 8A
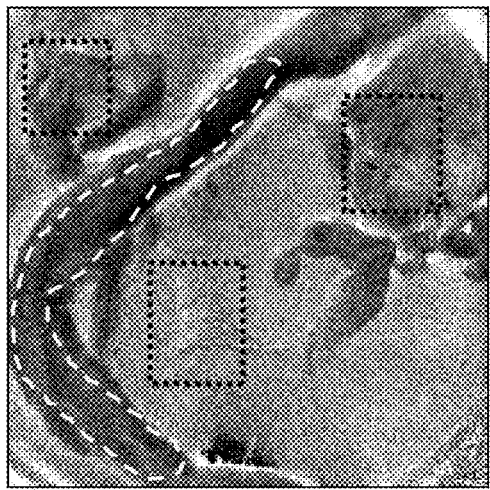
FIG. 8C
FIG. 8

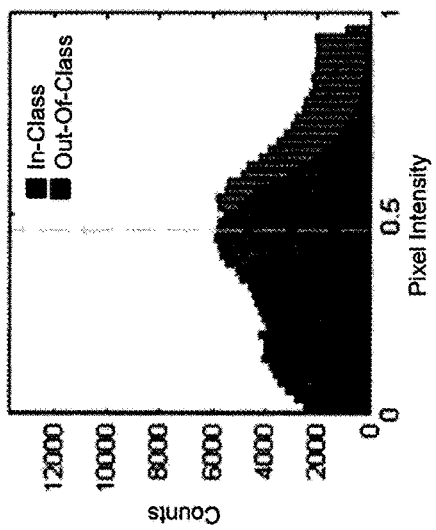
FIG. 9B
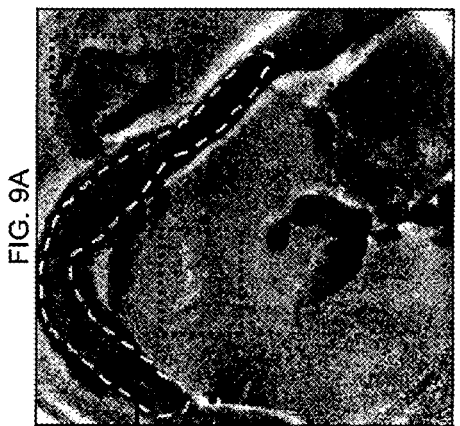
FIG. 9A
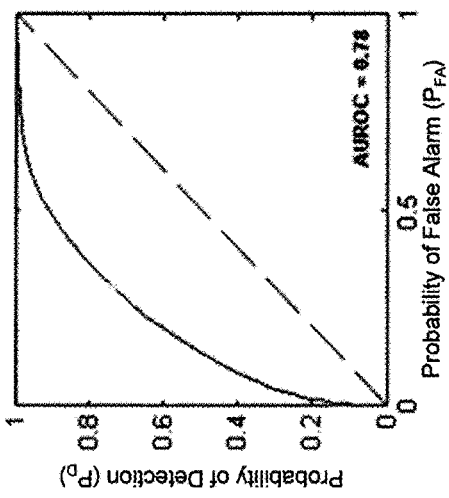
FIG. 9C
FIG. 9

FIG. 10B
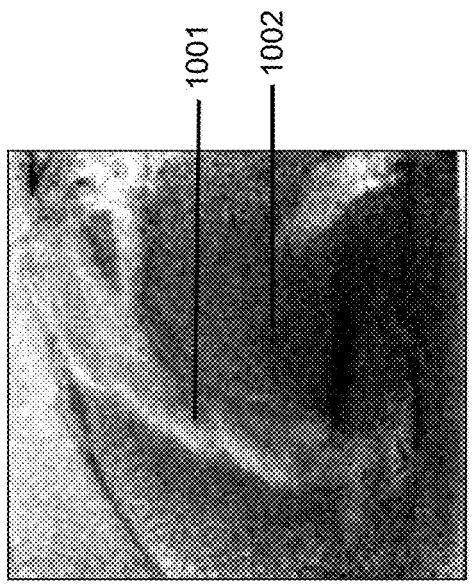
FIG. 10D
FIG. 10A
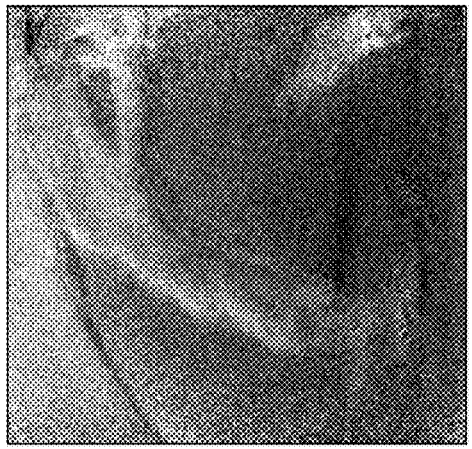
FIG. 10C
FIG. 10

FIG. 11B
FIG. 11C
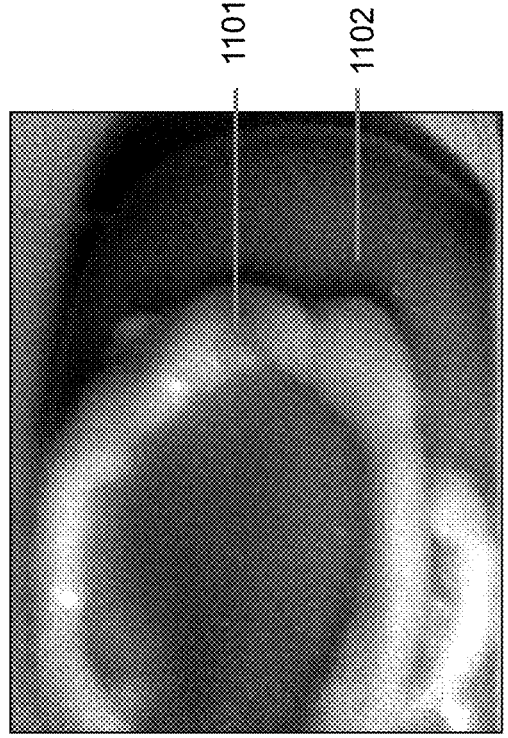
FIG. 11A
FIG. 11

SYSTEM AND METHOD FOR INTRAOPERATIVE DETECTION OF CANCER MARGINS USING CONFORMAL FILTERS IN A DUAL POLARIZATION CONFIGURATION

CROSS-REFERENCE TO RELATED APPLICATIONS

This application is a divisional of U.S. patent application Ser. No. 14/302,225 filed Jun. 11, 2014 and entitled "System and Method for Intraoperative Detection of Cancer Margins Using Conformal Filters in a Dual Polarization Configuration," which claims the priority benefit of U.S. Provisional Patent Application No. 61/833,622, filed Jun. 11, 2013 and entitled "System and Method for Intraoperative Detection of Cancer Margins Using Conformal Filters in a Dual Polarization Configuration," the contents of which are both incorporated herein by reference in their entirety.

BACKGROUND

Spectroscopic imaging combines digital imaging and molecular spectroscopy techniques including Raman scattering, fluorescence, photoluminescence, ultraviolet, visible and infrared absorption spectroscopies. When such techniques are applied to the chemical analysis of materials, spectroscopic imaging is commonly referred to as chemical imaging or molecular imaging. Instruments for performing spectroscopic, e.g. chemical, imaging typically comprise an illumination source, an image gathering optic, a focal plane array imaging detector and an image spectrometer.

Generally, the sample size determines the choice of image gathering optic. For example, a microscope is typically employed to analyze sub-micron to millimeter spatial dimension samples. In the case of larger objects, in the range of millimeter to meter dimensions, macro-lens optics are appropriate. For samples located within relatively inaccessible environments, flexible fiberscope or rigid borescopes may be employed. Further, for very large scale objects, such as planetary objects, telescopes are appropriate image gathering optics.

For detection of images formed by the various optical systems, two-dimensional, imaging focal plane array ("FPA") detectors are typically employed. The choice of FPA detectors is governed by the spectroscopic technique employed to characterize the sample of interest. For example, silicon (Si) charge-coupled device ("CCD") detectors or CMOS detectors are typically employed with visible wavelength fluorescence and Raman spectroscopic imaging systems, while indium gallium arsenide ("InGaAs") FPA detectors are typically employed with near-infrared spectroscopic imaging systems.

Spectroscopic imaging of a sample is commonly implemented by one of two methods. First, point-source illumination may be used on a sample to measure the spectrum at each point of the illuminated area. Second, spectra can be collected over the entire area encompassing a sample simultaneously using an electronically tunable optical imaging filter such as an acousto-optic tunable filter ("AOTF"), a multi-conjugate tunable filter ("MCF"), or a liquid crystal tunable filter ("LCTF"). Here, the organic material in such optical filters is actively aligned by applied voltages to produce the desired bandpass and transmission function. The spectrum obtained for each pixel of an image forms a complex data set referred to as a hyperspectral image. Hyperspectral images may contain the intensity values at numerous wavelengths or the wavelength dependence of each pixel element in the image. Multivariate routines, such as chemometric techniques, may be used to convert spectra to classifications.

Spectroscopic devices operate over a range of wavelengths dependent on the operation ranges of the detectors or tunable filters employed. The devices may operate and provide analysis in the Ultraviolet (UV), visible (VIS), near infrared (NIR), short-wave infrared (SWIR), midwave infrared (MWIR), and/or long wave infrared (LWIR) wavelength ranges, including some overlapping ranges. These ranges correspond to wavelengths of approximately 180-380 nm (UV), 380-700 nm (VIS), 700-2500 nm (NIR), 850-1800 nm (SWIR), 650-1100 nm (MWIR), 400-1100 nm (VIS-NIR) and 1200-2450 nm (LWIR).

A LCTF employs birefringent retarders to distribute the light energy of an input light signal over a range of polarization states. The polarization state of light emerging at the output of the LCTF is caused to vary as a function of wavelength due to differential retardation of the orthogonal components of light, contributed to by the birefringent retarders. The LCTF discriminates for wavelength-specific polarization using a polarizing filter at the output. The polarizing filter passes the light components through the output that are rotationally aligned to the polarizing filter. The LCTF is tuned by adjusting the birefringence of the retarders so that a specific discrimination wavelength that is aligned to the output polarizing filter emerges in a plane polarized state. Other wavelengths that emerge in other polarization states and/or alignments are attenuated.

A highly discriminating spectral filter is possible using a sequence of several birefringent retarders. The thicknesses, birefringences, and relative rotation angles of the retarders are chosen to correspond to the discrimination wavelength. More specifically, the input light signal to the filter becomes separated into orthogonal vector components, parallel to the respective ordinary and extraordinary axes of each birefringent retarder when encountered along the light transmission path through the filter. These separated vector components are differentially retarded due to the birefringence. Such differential retardation also amounts to a change in the polarization state. For a plane polarized component at the input to the filter, having a specific rotational alignment at the input to the filter and at specific discrimination wavelengths, the light components that have been divided and subdivided all emerge from the filter in the same polarization state and alignment, namely plane polarized and in alignment with the selection polarizer, i.e., the polarizing filter, at the output.

A filter as described is sometimes termed an interference filter due to the components being divided and subdivided from the input and interfering positively at the output selection polarizer are the components that are passed through the filter. Such filters are sometimes described with respect to a rotational twist in the plane polarization alignment of the discriminated component between the input and the selection polarizer at the output.

There are several known configurations of spectral filters comprising birefringent retarders and such filters include, for example, Lyot, Solc, and Evans types. These filters can be constructed with fixed (non-tunable) birefringent crystals as retarders. A filter with retarders that are tuned in unison will permit adjustment of the bandpass wavelength. Tunable retarders can comprise liquid crystals or composite retarder elements, each comprising a fixed crystal and an optically aligned liquid crystal.

The birefringences and rotation angles of the retarders are coordinated such that each retarder contributes part of the necessary change in polarization state to alter the polarization state of the passband wavelength from an input reference angle to an output reference angle. The input reference angle may be, for example, 45° to the ordinary and extraordinary axes of a first retarder in the filter. The output reference angle is the rotational alignment of the polarizing filter, i.e., "selection polarizer."

A spectral filter may have a comb-shaped transmission characteristic. Increasing or decreasing the birefringence while tuning to select the discrimination wavelength (or passband), stretches or compresses the comb shape of the transmission characteristic along the wavelength coordinate axis.

If the input light is randomly polarized, the portion that is spectrally filtered is limited to the vector components of the input wavelengths that are parallel to one of the two orthogonal polarization components that are present. Only light at the specific wavelength, and at a given reference polarization alignment at the input, can emerge with a polarization angle aligned to the rotational alignment of the selection polarizer at the output. The light energy that is orthogonal to the reference alignment at the input, including light at the passband wavelength, is substantially blocked.

Currently, tunable optical filter technology is limited to single bandpass, low throughput operation and passes only one of two orthogonal components of input light. The transmission ratio in the passband is at a maximum for incident light at the input to the LCTF that is aligned to a reference angle of the LCTF. Transmission is at a minimum for incident light energy at the input that is orthogonal to that reference angle. If the input light in the passband is randomly polarized, the best possible transmission ratio in the passband is fifty percent. In addition, multiple discrete bandpass measurements are required for tissue type discrimination. The need for multiple measurements translates directly into overall measurement time.

Multivariate Optical Computing is an approach which utilizes a compressive sensing device, e.g. an optical computer, to analyze spectroscopic data as it is collected. Other approaches utilize hard coated optical computing filters such as Multivariate Optical Elements ("MOEs"). MOEs are application-specific optical thin film filters that are used in transmission and reflectance modes. The radiometric response of a MOE-based instrument is proportional to the intended tissue type in an associated matrix. While compressive sensing holds potential for decreasing measurement time, the use of MOEs has limitations. For example, MOEs are fixed and lack flexibility for adapting to different tissue types.

Cancer is an enormous global health burden, accounting for one in every eight deaths worldwide. A critical problem in cancer management is the local recurrence of disease, which is often a result of incomplete excision of the tumor. Currently, tumor margins must be identified through histological evaluation of an affected tissue biopsy post-surgery. As such, approximately one in four patients who undergo tumor resection surgery will require a follow-up operation in order to fully excise the malignant tissue. Recent efforts aimed towards significantly reducing the frequency of local recurrence have employed diffuse reflectance, radiofrequency spectroscopy, and targeted fluorescence imaging. However, there remains an urgent need to develop a highly specific and sensitive tool to detect features in biological tissues, including intraoperative real-time tumor margin detection methods that will reduce the risk of cancer recurrence and the need for subsequent operations.

Current techniques for gross anatomic pathology require inspection by a pathologist and are therefore inherently subjective. There exists a need for a system and method that would enable objective analysis of organ samples and other biological tissues. It would also be advantageous if such a system and method were designed as an intra-operative tool, providing both molecular and spatial information. There exists a need for an adaptable filter that can be used to detect a wide variety of tissue types while reducing overall measurement time. It would be advantageous if the filter could be incorporated into a system for biomedical applications such as intraoperative applications.

SUMMARY

Some embodiments are, individually and collectively, directed devices, systems that include an intraoperative optical diagnostic device configured to detect features of a biological sample. The intraoperative optical diagnostic device may include an optical separator positioned to receive interacted photons from the biological sample and configured to separate the interacted photons into a first optical path and a second optical path; a first conformal filter positioned to receive interacted photons from the first optical path, the first conformal filter having one or more filter stages configured to filter the interacted photons in the first optical path and generate a first filtered component; a second conformal filter positioned to receive interacted photons from the second optical path, the second conformal filter having one or more filter stages configured to filter the second optical component and generate a second filtered component; a controller operably connected to the first conformal filter and the second conformal filter, the controller being configured to apply voltage to each of the one or more filter stages of the first conformal filter and each of the one or more filter stages of the second conformal filter; and one or more detectors positioned to receive the first filtered component, the second filtered component or combinations thereof, each of the one or more detectors being configured to detect the first filtered component, the second filtered component, and combinations there and generate image data from the first filtered component, the second filtered component, or combinations thereof. The systems and methods of various embodiments may further include a processor operably connected to each of the one or more detectors and the controller, the processor being configured to analyze the image data and generate images related thereto, the processor further being capable of causing the controller to individually apply voltage to each stage of each of the first conformal filter and the second conformal thereby individually tuning the each of the first conformal filter and second conformal filter.

In some embodiments, the one or more filter stages of the first conformal filter and the one or more filter stages of the second conformal filter comprise a tunable filter. In certain embodiments, each of the first conformal filter and second conformal filter may individually include one or more of a liquid crystal tunable filter, an acousto optical tunable filter, a Lyot liquid crystal tunable filter, an Evans Split-Element liquid crystal tunable filter, a Solc liquid crystal tunable filter, a Ferroelectric liquid crystal tunable filter, and a Fabry Perot liquid crystal tunable filter. In particular embodiments, the each of the first conformal filter and second conformal filter individually include a multi-conjugate tunable filter.

In some embodiments, the controller may be configured to apply one or more voltages to each of the filter stages of the first conformal filter and to each of the filter stages of the second conformal filter which cause the first conformal filter to conform to a spectral shape associated with a first analyte and the second conformal filter to conform to a spectral shape associated with a second analyte. The first analyte and the second analyte in such embodiments, can be the same, or the first analyte and the second analyte can be different. In certain embodiments, a Look Up Table ("LUT") may be in operable communication with the processor, and the LUT may include one or more voltages associated with each stage of the one or more stages of the first conformal filter and each stage of the one or more stages of the second conformal filter and each voltage may configure each stage of the first conformal filter and each stage of the second conformal filter to a spectral shape associated with the one or more analytes. In certain embodiments, the controller may be configured to apply the one or more voltages to the one or more stages of the first conformal filter and the one or more stages of the second formal filter while image data is collected.

In various embodiments, the one or more detectors may include a first detector configured to detect the first filtered component and a second detector configured to detect the second filtered component. In other embodiments, the one or more detectors may include one detector configured to detect the first filtered component and the second filtered component. In some embodiments, the first filtered component and the second filtered component are detected simultaneously, and in other embodiments, the first filtered component and the second filtered component are detected sequentially.

The image data may include a first data set generated from the first filtered component and a second data second generated from the second filtered component. In some embodiments, the first test data set may include a target analyte of the one or more analytes and the second data set may represent a matrix including one or more non-target analytes. Each of the one or more test data sets can include one or more of a VIS data set, a NIR data set, and a SWIR data set.

In some embodiments, the devices and systems may further include one or more of a robotic instrument and a laparoscopic instrument.

The devices, systems, and methods described above may be used to distinguish between different tissues. For example, in some embodiments, the one or more features of the biological tissue may include one or more of an anatomical feature, a normal tissue, an abnormal tissue, a tumor, a tumor margin, a large organ section and a surgical margin. In particular embodiments, the biological sample may include one or more of kidney tissue, heart tissue, breast tissue, ovarian tissue, lung tissue, liver tissue, bladder tissue, intestinal tissue, stomach tissue, cornea tissue, lens tissue, bone tissue, and skin tissue.

In certain embodiments, the devices and systems may further include a non-transitory storage medium in operable communication with the processor, and the storage medium may include one or more programming instructions that, when executed, causes the processor to do the following:
  direct the controller to apply one or more voltages to the one or more stages of the first conformal filter to tune the first conformal filter to a first configuration;
  direct the controller to apply one or more voltages to the one or more stages of the second conformal filter to tune the second conformal filter to a second configuration;
  generate the one or more test data sets; and
  analyze the one or more test data sets.

In some embodiments, the storage medium may further include one or more programming instructions that, when executed, cause the processor to:
  select the first configuration from a LUT comprising the one or more analytes, wherein the LUT comprises one or more voltages associated with the one or more stages of the first conformal filter to configure the first conformal filter to a first analyte; and
  select the second configuration from a LUT comprising the one or more analytes, wherein the LUT comprises one or more voltages associated with the one or more stages of the second conformal filter to configure the second conformal filter to a second analyte.

In such embodiments, the first configuration may be a configuration for detecting one or more target analytes from the one or more analytes and the second configuration may include a configuration for detecting a matrix comprising one or more non-target analytes from the one or more analytes. In particular embodiments, the storage medium may further include instructions that, when executed, cause the processor to apply one or more chemometric techniques to the one or more test data sets.

Particular embodiments are directed to methods for detecting one or more features of a biological tissue that include the steps of: separating interacted photons comprising photons that have interacted with one or more analytes in the biological sample into a first optical component and a second optical component; passing the first optical component through a first conformal filter comprising one or more filter stages and generating a first filtered component; passing the second optical component through a second conformal filter comprising one or more filter stages and generating a second filtered component; applying one or more voltages to the one or more stages of the first conformal filter and to the one or more stages of the second conformal filter; detecting the first filtered component and the second filtered component and generating one or more test data sets; and analyzing the one or more test data sets with a computer processor to detect the features of the biological tissue.

In some embodiments, applying one or more voltages to the one or more filter stages of the first conformal filter and to the one or more stages of the second conformal filter may configure the first conformal filter to conform to a spectral shape associated with a first analyte and may configure the second conformal filter to conform to a spectral shape associated with a second analyte. In some embodiments, applying the one or more voltages, may further include referencing a LUT comprising one or more voltages associated with each stage of the one or more stages of the first conformal filter and each stage of the one or more stages of the second conformal filter, wherein the one or more voltages applied to the first conformal filter configures the first conformal filter to a spectral shape of a first analyte and the one or more voltages applied to each stage of the second conformal filter configures the second conformal filter to a spectral shape associated with second.

In various embodiments, the one or more features of the biological tissue may be one or more of an anatomical feature, a normal tissue, an abnormal tissue, a tumor, a tumor margin, a large organ section and a surgical margin. In some embodiments, the first analyte and the second analyte can be the same, and in other embodiments, the first analyte and the second analyte may be different. In some embodiments, the first filtered component and the second filtered component may be detected by the same detector, and in other embodiments, the filtered component and the second filtered component may be detected by a plurality of detectors. In some embodiments, the first filtered component and the second filtered component may be detected simultaneously, and in other embodiments, the first filtered component and the second filtered component may be detected sequentially.

In certain embodiments, the one or more voltages can be applied to the one or more stages of the first conformal filter and to the one or more stages of the second conformal filter actively.

In some embodiments, the one or more test data sets may include a first test data set generated from the first conformal filter and a second test data set generated from the second conformal filter. In such embodiments, the first data set may represent the one or more target analytes of the one or more analytes and the second data set may represent a matrix comprising one or more non-target analytes of the one or more analytes. In certain embodiments, the biological sample may be one or more of kidney tissue, heart tissue, breast tissue, ovarian tissue, lung tissue, liver tissue, bladder tissue, intestinal tissue, stomach tissue, cornea tissue, lens tissue, bone tissue, and skin tissue. In various embodiments, the one or more test data sets may include one or more of a VIS data set, a NIR data set, and a SWIR data set.

In some embodiments, the step of analyzing may further include applying one or more optical computations to the one or more test data sets. In certain embodiments, the optical computation may include one or more of T1, T1-T2 and (T1-T2)/(T1+T2).

In some embodiments, the methods may further include:
  directing the controller to apply the one or more voltages to the one or more stages of the first conformal filter to tune the first conformal filter to a first configuration; and
  directing the controller to apply the one or more voltages to the one or more stages of the second conformal filter to tune the second conformal filter to a second configuration.
In certain embodiments, the method may further include:
  selecting the first configuration from a LUT comprising the one or more analytes, wherein the LUT comprises more or more voltages associated with the one or more stages of the first conformal filter to configure the first conformal filter to a first analyte; and
  selecting the second configuration by consulting a LUT comprising the one or more analytes, wherein the LUT comprises more or more voltages associated with the one or more stages of the second conformal filter to configure the second conformal filter to a second analyte.

In some embodiments, the first configuration may include a configuration for detecting one or more target analytes from the one or more analytes and the second configuration comprises a configuration for detecting a matrix comprising one or more non-target analytes from the one or more analytes. In certain embodiments, the step of analyzing may further include applying one or more chemometric techniques to the one or more test data sets.

BRIEF DESCRIPTION OF THE FIGURES

The accompanying drawings, which are included to provide further understanding of the disclosure and are incorporated in and constitute a part of this specification illustrate embodiments of the disclosure, and together with the description, serve to explain the principles of the disclosure.

FIG. 6 is representative of the detection capabilities on a kidney sample according to an embodiment;

FIG. 7 is representative of the detection capabilities on a kidney sample according to a second embodiment;

FIG. 8 is illustrative of the detection capabilities according to an embodiment;

FIG. 9 is illustrative of the detection capabilities according to a second embodiment;

FIG. 10 is illustrative of the enhanced contrast achieved according to an embodiment; and FIG. 11 is illustrative of improved contrast achieved on a kidney sample according to an embodiment.

DETAILED DESCRIPTION

Figure 1:
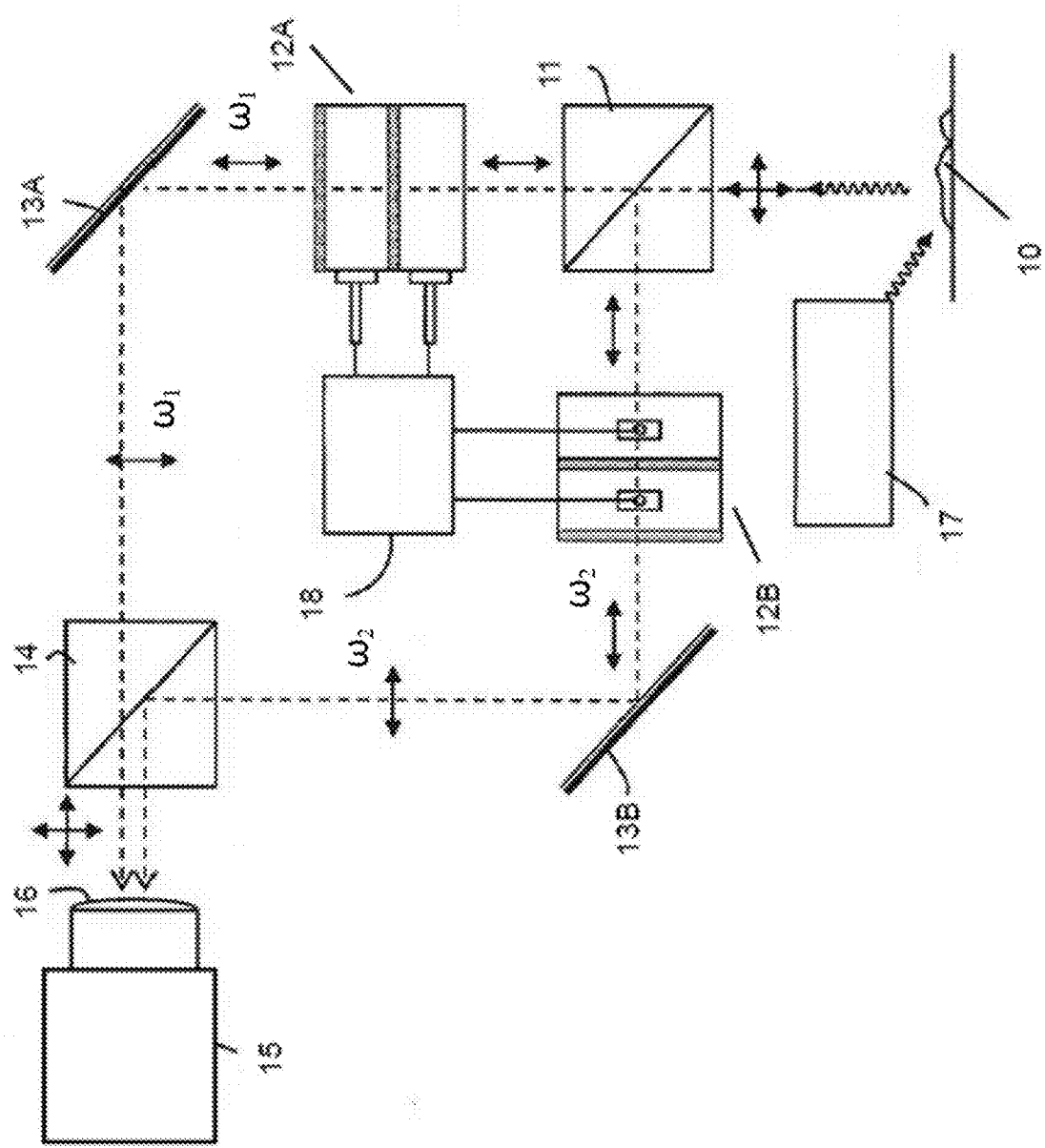
FIG. 1 is a schematic representation of an intraoperative optical diagnostic device according to an embodiment.

Reference will now be made in detail to the embodiments of the present disclosure, examples of which are illustrated in the accompanying drawings. Wherever possible, the same reference numbers will be used throughout the specification to refer to the same or like parts.

Unless defined otherwise, all technical and scientific terms have the same meaning as is commonly understood by one of ordinary skill in the art to which the embodiments disclosed belongs.

As used herein, "a" or "an" means "at least one" or "one or more."

As used herein, "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

"Optional" or "optionally" may be taken to mean that the subsequently described structure, event or circumstance may or may not occur, and that the description includes instances where the event occurs and instances where it does not.

The term "tissue" refers to an aggregate of morphologically similar cells with associated intercellular matter that may act together to perform one or more specific functions in the body of an organism including a human. The term "tissue" also encompasses organs comprising one or more tissue types.

Various embodiments of the invention are directed to intraoperative optical diagnostic devices and systems for detecting the features of biological samples that include interopertive optical diagnostic devices. Further embodiments are directed to methods for using such devices and systems. The intraoperative optical diagnostic devices of such embodiments are capable of detecting morphological and biochemical differences in the biological samples that are not visually detectable and are unlikely to be detected using current standard devices and techniques. For example, in certain embodiments, the intraoperative optical diagnostic devices and systems incorporating these devices can be used to distinguish a particular tissue type from neighboring tissues thereby delineating the margins between these tissues. In particular embodiments, the intraoperative optical diagnostic devices and systems incorporating these devices can be used to distinguish healthy tissue from diseased tissue, and in some embodiments the diseased tissue may be cancerous tissue or tumor. The use of these devices during surgery may provide the operating surgeon with real time visual information showing the margins of the diseased tissue.

The intraoperative optical diagnostic devices of various embodiments may at least include an optical separator positioned to receive light reflected from the biological tissue (i.e., interacted photons, which can include photons reflected by a sample, photons scattered by a sample, and photons emitted by a sample) and separate the interacted photons into at least two optical paths. Although the devices of such embodiments can include more than two optical paths, for simplicity such embodiments are referred to as "dual polarization" devices. Each optical path may include one or more filters that reflect interacted photons of particular wavelengths removing them from the optical path and allow other interacted photons to pass through the filter generating filtered interacted photons, i.e. a "filtered component." In some embodiments, each optical path may terminate in a detector which is positioned to receive and detect the filtered component. In other embodiments, a single detector may be positioned to simultaneously receive and detect the filtered components from each optical path. Thus, embodiments may include one or more detectors depending on the configuration. The intraoperative optical devices of such embodiments including one or more detectors may further include a processor electronically connected to the one or more detectors that receive data from the detector. The processor may be configured to analyze the data and generate an image of the biological sample, and in certain embodiments, the image may clearly show the boundaries of different tissue types in the biological sample.

Figure 2:
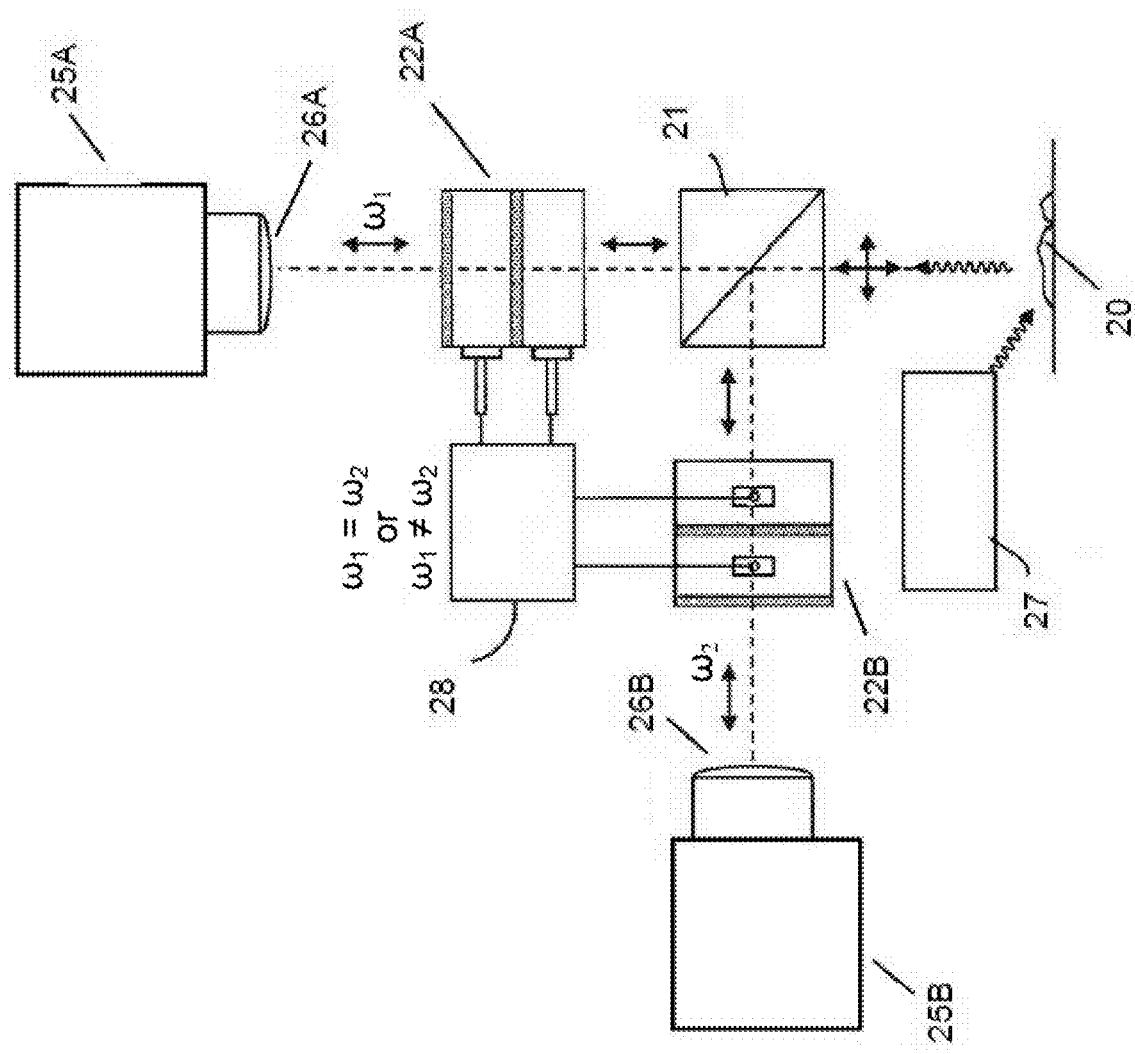
FIG. 2 is a schematic representation of an intraoperative optical diagnostic device according to a second embodiment.

Schematics of examples of intraoperative optical diagnostic devices are provided in FIG. 1 and FIG. 2. FIG. 1 represents a device having an optical separator 11 positioned to receive light from a sample 10 and split the received light into two optical paths (illustrated by hashed lines). In particular embodiments, the optical separator 11 may be a polarizing beamsplitter that redirects received light along distinct orthogonal beam paths. Filters 12A, 12B are positioned along each optical path to receive and filter the split light. In the configuration of FIG. 1, after passing through the filter 12A, 12B, the filtered beams travel along their respective optical paths to reflectors (e.g., mirrors) 13A, 13B to a combiner 14 such as a polarizing cube or polarizing beam splitter where the optical paths are combined and directed toward a detector 15, which may include, among other things, a lens 16. In some embodiments, the optical paths may be directed to the detector 15 separately; however, the optical paths from optical separator 11 to the combiner 14 should be symmetrical to avoid, for example, the need for corrective optics.

FIG. 2 is a schematic of another example of intraoperative optical diagnostic devices of the invention. In the configuration shown in FIG. 2, two detectors 25A, 25B are illustrated. Like the configuration illustrated in FIG. 1, an optical separator 21 is positioned to receive light from a sample 20 and split the received light into two optical paths (illustrated by hashed lines). Filters 22A, 22B are positioned along each optical path to receive and filter the split light. Unlike the configuration of FIG. 1, after passing through the filter 12A, 12B, each of the filtered beams travels along its respective optical path to an independent detector 25A, 25B, which can include a lens 26A, 26B, to capture filtered signals from each filter 22A, 22B. In some embodiments, the two filtered signals may be detected simultaneously, which could allow for real-time detection when displayed in a non-overlapping configuration (side-by-side, top to bottom, etc.). In other embodiments, the two filtered signals may be detected sequentially.

In some embodiments, the intraoperative optical diagnostic devices, such as those illustrated in FIG. 1 and FIG. 2, may include an illumination/excitation source 17, 27, such as a spot light or laser. In other embodiments, the source light may be a passive light source, for example, in the case of intraoperative devices, lights used to illuminate an operating room or spotlights positioned by the operating physician or surgical assistant to illuminate the tissue for visual observation. The illumination/excitation source 17, 27 may be positioned to illuminate the biological sample 10, 20 directly, or in some embodiments, the illumination/excitation source 17, 27 may direct light, for example, from an oblique angle to the biological sample 10, 20. Notably, although light irradiating the sample 10, 20, for example, by a laser, may be coherent, the light received from the sample 10, 20 (e.g., emitted, scattered, and/or reflected light) and fed to the filters 12A, 12B, 22A, 22B may not be coherent.

In some embodiments, the filters 12A, 12B, 22A, 22B may be tuned to a filter having a particular spectral shape. In other embodiments, the filters 12A, 12B, 22A, 22B may be tuned between uses or while the device is in use. In such embodiments, the intraoperative optical diagnostic devices may include one or more controllers 18, 28. The one or more controllers 18, 28 may be operably connected to each filter 12A, 12B, 22A, 22B, and may be configured to tune each filter independently or in unison. Therefore, by appropriate control, the filters 12A, 12B, 22A, 22B may be tuned to the same spectral shape or to two different spectral shapes at the same time. For example, one filter 12A, 22A may be tuned to a configuration for detecting a first tissue type, and the other filter 12B, 22B may be tuned to detect a second tissue type. In various embodiments, the first tissue type may be healthy tissue, which can be referred to as a "matrix." The second tissue type may be diseased tissue, such as a tumor, and the filter associated with the second tissue type may be tuned or configured to detect a tissue type associated with the disease state. For example, the second tissue type may be cancerous or tumor tissue which expresses a protein or contains a tissue component that is not present in healthy tissue. The controller 18, 28 may be programmable or implemented in software to allow a user to selectively tune each filters 12A, 12B, 22A, 22B.

The detectors 15, 25A, 25B of various embodiments may be any type of detector known in the art. For example, in some embodiments, each detector 15, 25A, 25B may be a charge coupled device (CCD), a complementary metal-oxide-semiconductor (CMOS) detector, an indium gallium arsenide detector, a platinum silicide detector, an indium antimonide detector, a mercury cadmium telluride detector, or any combination thereof. In certain embodiments, each detector 15, 25A, 25B may be a CCD or CMOS detector.

The intraoperative optical diagnostic devices described above may include a processor or a means for connecting to a processor. In such embodiments, the processor may operably connect to at least the detectors 15, 25A, 25B, and in certain embodiments, the detectors 15, 25A, 25B and the controller 18, 28. The processor may be configured to receive data relating to the filtered light from each detector 15, 25A, 25B and use this data to generate an image and display the image on a display device.

In some embodiments, the processor may generate a single image that is displayed on the display device, and in other embodiments, the processor may generate multiple images based on the data acquired from each detector 15, 25A, 25B. In still other embodiments, the device may include a fast switching mechanism to switch between the two views (or spectral images) corresponding to spectral data collected by the detector 15, 25A, 25B from each of the filters 12A, 12B, 22A, 22B. When a single image is displayed, the image may be generated from spectral data obtained from one filter 12A, 12B, 22A, 22B, or the spectral data may be combined or overlaid into a single image, which may provide increased contrast or intensity or provide a comparison. In other embodiments, separate images corresponding with the data obtained from each filter 12A, 12B, 22A, 22B may be displayed side-by-side.

In some embodiments, the processor may be in communication with a non-transitory, computer readable storage medium containing a look-up table ("LUT"). The LUT may include information that allows the filter to be tuned to detect particular tissue types associated with particular diseased states. For example, a LUT may include a number of voltages that when applied to a filter 12A, 12B, 22A, 22B allow the filter to produce filtered light of a spectral shape associated with one or more tissue types related to various diseased states. In the case of a multi-stage filter, the LUT may include voltages that can be applied to each stage in order to produce filtered light associated with tissue types related to various diseased states.

In embodiments including a LUT, the processor may acquire the appropriate information from the LUT based on user input or image processing. The processor may then communicate this information to the controller 18, 28, which in turn applies the appropriate voltages to each filter 12A, 12B, 22A, 22B or each stage in each filter. In some embodiments, this process may occur in or in near real time providing flexibility for detecting multiple tissue types of interest in near real time. This may allow the user to modify or completely change the displayed image while the intraoperative optical diagnostic device is in use.

Embodiments are not limited to particular filters. For example, each filter 12A, 12B, 22A, 22B may be a multi-conjugate liquid crystal tunable filter, an acousto-optical tunable filter, a Lyot liquid crystal tunable filter, an Evans split-element liquid crystal tunable filter, a Solc liquid crystal tunable filter, a ferroelectric liquid crystal tunable filter, or a Fabry Perot liquid crystal tunable filter, and in some embodiments, each optical path may include a combination of such filters. In certain embodiments, each filter 12A, 12B, 22A, 22B may include a modified liquid crystal tunable filter and a liquid crystal tunable filter. In particular embodiments, each filter 12A, 12B, 22A, 22B of the device may be independently tunable.

In certain embodiments, each filter 12A, 12B, 22A, 22B may independently be a conformal filter. The term "conformal filter" refers to filters that simultaneously transmit multiple passbands, i.e., spectral shapes. The use of conformal filters improves discrimination performance for tissue types by, for example, discriminating between a target tissue type and background, and increases the throughput of a tunable filter, thereby, improving the speed of an analysis. The conformal filters, which are traditionally intended for single bandpass transmission, may be tunable to enable tuning to a variety of different configurations. A number of filter types can be used as conformal filters and are encompassed by the filters 12A, 12B, 22A, 22B described above. Examples of tunable filters that may be configured for use as a conformal filter may include, but are not limited to, a liquid crystal tunable filter, an acoustic optical tunable filter, a Lyot liquid crystal tunable filter, an Evans Split-Element liquid crystal tunable filter, a Solc liquid crystal tunable filter, a Ferroelectric liquid crystal tunable filter, a Fabry Perot liquid crystal tunable filter, and combinations thereof.

In particular embodiments, the tunable filter may be a magnetically coupled filter (MCF), which can include successive stages along an optical path, and in some embodiments, each stage may be configured as a Solc filter. Angularly distributed retarder elements of equal birefringence are stacked in each stage with a polarizer between stages. The retarders can include tunable (such as abutted liquid crystals), fixed and/or combined tunable and fixed birefringences. In some embodiments, the retarders may be quartz retarders. Although the retardations are equal within each stage, distinctly different retardations may be used for two or more different stages. This causes some stages to pass narrow bandpass peaks and other stages to have widely spaced bandpass peaks. The transmission functions of the serial stages are superimposed with selected tunable peaks coinciding. The resulting conjugate filter has a high finesse ratio and good out of band rejection. As discussed above, conformal filter configurations may be determined by consulting the LUT, which includes information corresponding with the conformal figure configuration necessary to obtain filtered light that can be used to detect various tissue types. The LUT may comprise at least one voltage associated with each stage of the tunable filter. These voltages may be such that when applied to the associated stage, the tunable filter conforms to a spectral shape associated with the tissue type. LUTs may be modified, to provide the appropriate conformal filter configurations for detecting a variety of different tissue types.

In various embodiments, the conformal filters 12A, 12B, 22A, 22B may be tuned to filter interacted photons that conform to the same spectral shapes. In other embodiments, the conformal filters 12A, 12B, 22A, 22B may be tuned to filter interacted photons that conform to different spectral shapes. A system including conformal filters 12A, 12B, 22A, 22B tuned to filter different spectral shapes can be used to simultaneous analyze a biological tissue for a plurality of tissue components of interest.

Figure 3:
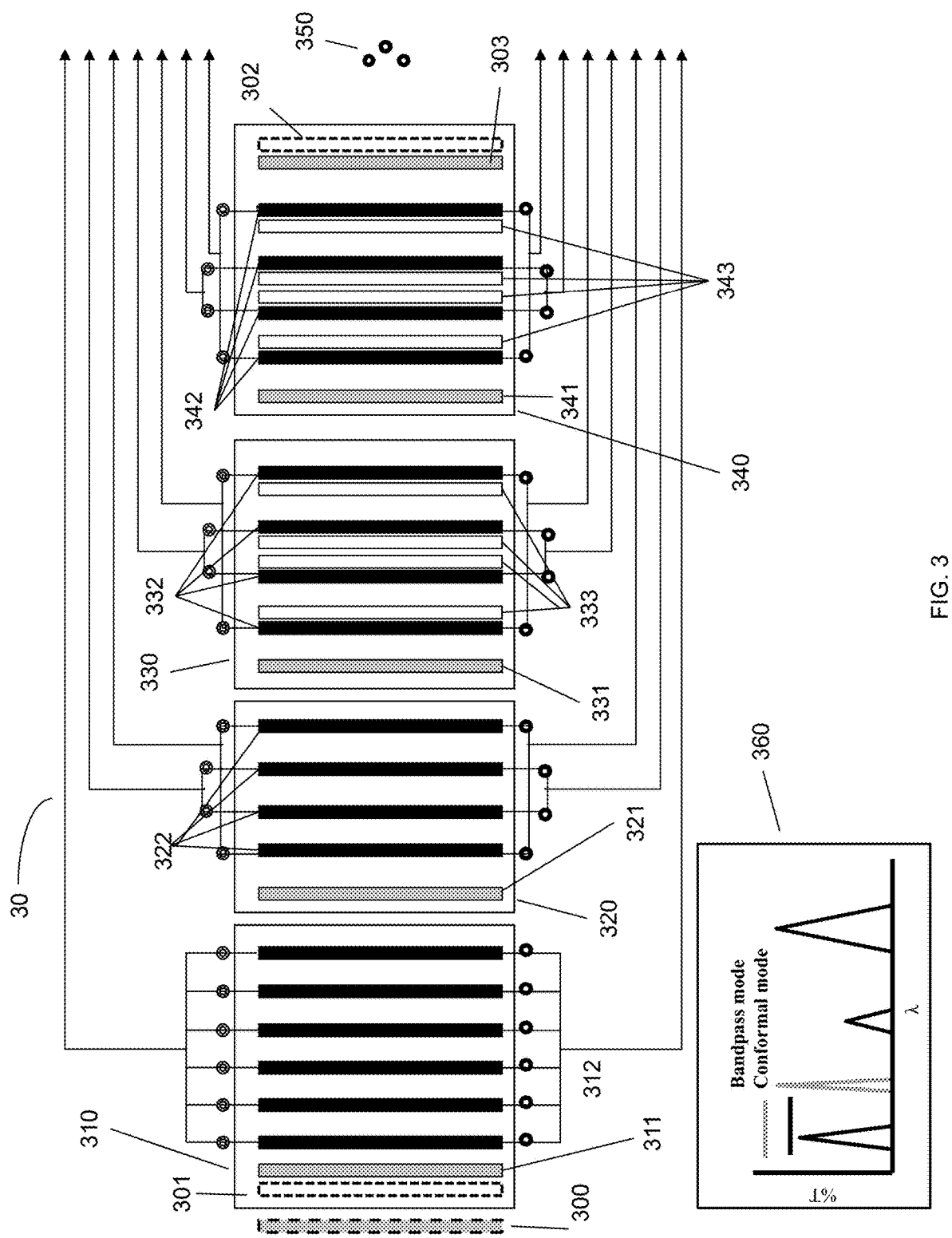
FIG. 3 is a schematic representation of a conformal filter according to an embodiment.
Figure 4:
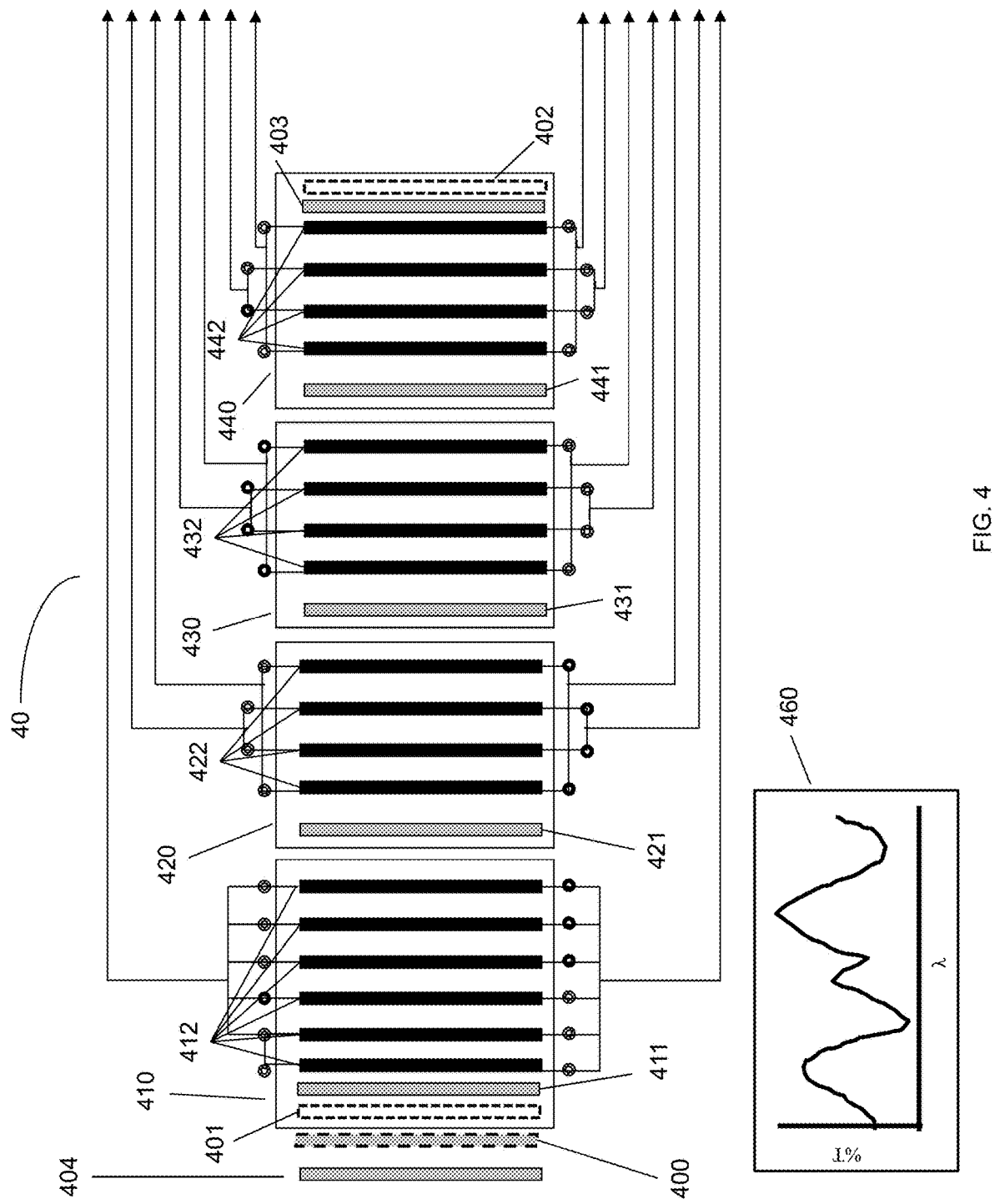
FIG. 4 is a schematic representation of a conformal filter according to a second embodiment.
Figure 5:
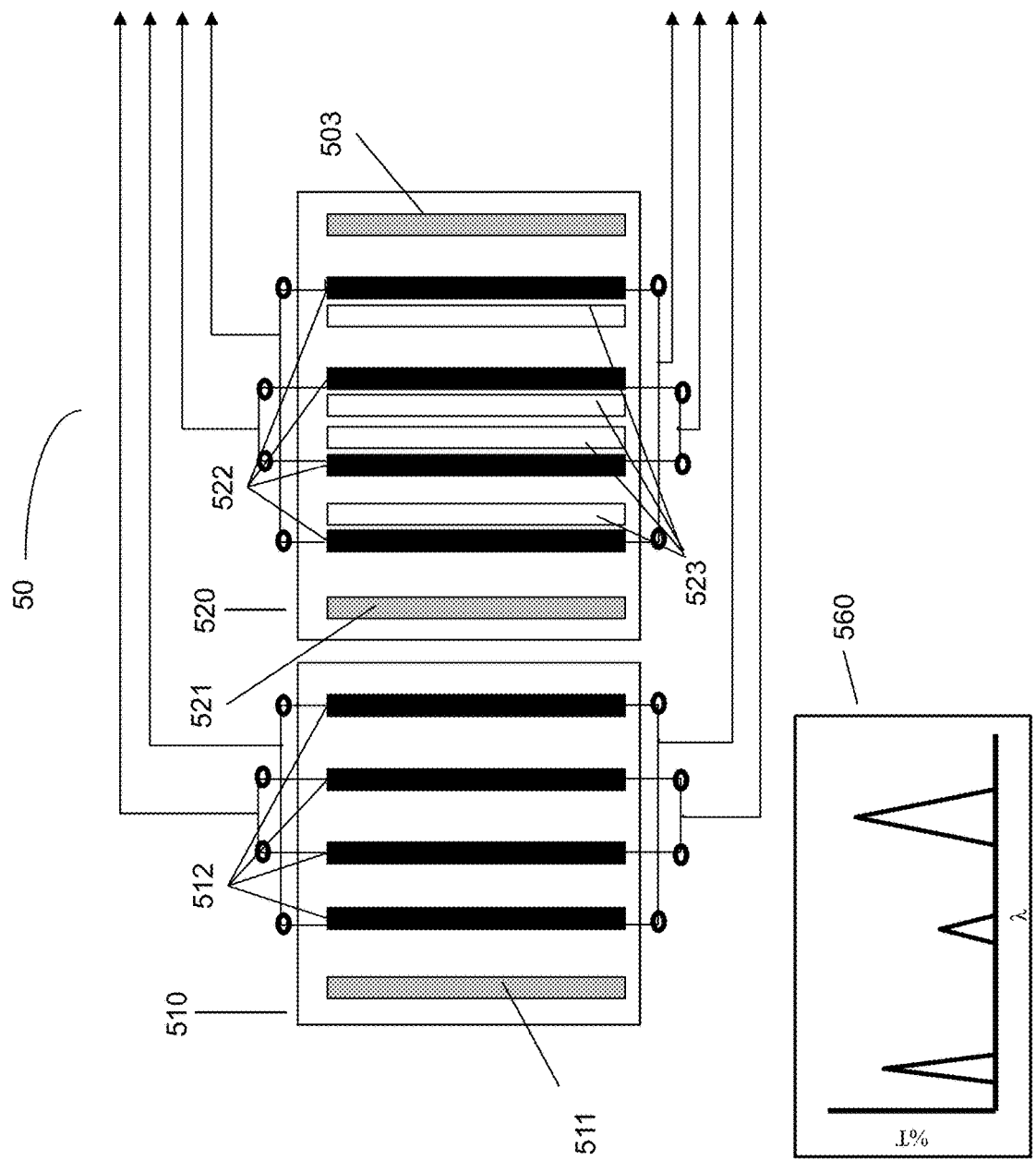
FIG. 5 is a schematic representation of a conformal filter according to a third embodiment.

FIGS. 3-5 are schematics of conformal filters that can be incorporated into the intraoperative optical diagnostic devices of various embodiments described above.

FIG. 3 shows a conformal filter 30 that includes a hot mirror 300 and may be operably connected to a plurality of filter stages, such as a first stage 310, a second stage 320, a third stage 330, and a fourth stage 340. Each stage 310, 320, 330, 340 is arranged in a Solc configuration including a polarizer 311, 321, 331, 341 upstream from a combination of liquid crystal cells 312, 322, 332, 342. In stages three 330 and four 340, quartz retarders 333 and 343 are interspersed between the liquid crystal cells of the combination of liquid crystal cells 332 and 342. An input antireflective (AR) glass component 301 is disposed upstream of the first polarizer 311, and an output AR glass component 302 is disposed downstream of an output polarizer 303. The conformal filter 30 may further include a temperature sensor 350 for monitoring the temperature of the filter. A graph showing the predicted percent transmission (% T) as a function of wavelength (λ) of a filter configured 30 as described in FIG. 3 operating in both a bandpass and a conformal mode is provided in the inset graph 360.

FIG. 4 shows a conformal filter 40 having a similar configuration to the conformal filter 30 of FIG. 3 with the addition of an input polarizer 404 upstream of the hot mirror 400. In some embodiments, the input polarizer 404 may be a mechanically rotatable polarizer or an electronically tunable liquid crystal cell, and in certain embodiments, the input polarizer 404 may be mounted to a rotatable aperture for increasing optical throughput. The input polarizer 404 may be tuned with each individual filter stage 410, 420, 430, 440, or the input polarizer 404 may be tuned simultaneously with all of the filter stages 410, 420, 430, 440. In still other embodiments, the input polarizer 404 may be tuned separately. In addition, the conformal filter 40 of FIG. 4 does not include retarders. Like the conformal filter 30 of FIG. 3, each filter stage 410, 420, 430, 440 may include polarizers 411, 421, 431, 441 and liquid crystal cells 412, 422, 432, 442. An input antireflective (AR) glass component 401 may be positioned upstream of the first filter stage 410 polarizer 411, and an output AR glass component 402 may be positioned downstream of an output polarizer 403. A graph showing the predicted percent transmission (% T) as a function of wavelength ($\lambda$) of a filter configured 40 as described in FIG. 4 operating in both a bandpass and a conformal mode is provided in the inset graph 460.

In particular embodiments, tunable filters may be modified or specifically designed so that selected individual stages of a traditional tunable filter include multiple, lower resolution liquid crystal cells. Such a configuration is illustrated by FIG. 5, which shows an conformal filter 50 having fewer stages 510, 520. Each filter stage 510, 520 includes a polarizer 511, 521 and combination of liquid crystal cells 512, 522, and the second stage 520 includes quartz retarders 523 interspersed between the liquid crystal cells 522. As in the conformal filters 30, 40 of FIG. 3 and FIG. 4, the conformal filter 50 of FIG. 5 may also include an output polarizer 503. Other components, such as a hot mirror, input AR glass, output AR glass, input polarizers, and the like, not depicted in FIG. 5, may also be incorporated into conformal filters such as the conformal filter 50 illustrated in FIG. 5. A graph showing the predicted percent transmission as a function of wavelength ($\lambda$) of a conformal filter 50 configured as described in FIG. 5 operating in conformal mode is provided in the inset graph 560.

The embodiments are not intended to be limited to the designs described in FIG. 3-5. Recent advances in genomics and proteomics have identified a large number of molecules and signaling pathways that could potentially promote or limit diseases such as cancer, atherosclerosis, and infectious disease. Due to the sensitivity of molecular imaging to such changes, tissue types associated with cancer and non-cancerous healthy tissue can be identified.

The processor can be configured in any way and can manipulate and analyze the raw image data obtained from the one or more detectors in any way. In some embodiments, the processor may utilize Multivariate Optical Computing (MOC) techniques. Compressive sensing is the process in which a fully resolved waveform or image is reconstructed from a small set of sparse measurements using the redundancy in information across the sampled signal similar to lossy compression algorithms utilized for digital data storage. A fully expanded data set may be created through the solution of an undetermined linear system, which is an equation where the compressive measurements collected are smaller than the size of the original waveform or image. Compressive measurements may increase the rate at which image data is analyzed while preserving most of the original spectroscopic and spatial information contained in a molecular image collected over the full spectrum. Real-time Contrast Enhancement (RtCE) is the algorithmic optimization of dual polarization conformal filter measurements designed to produce an optical transmission function for analytical response. By employing conformal filter technology in conjunction with RtCE, fewer high throughput measurements would be required to achieve tissue type specificity such as tumor margin detection at a faster measurement time when compared to current imaging methods.

For example, as shown in FIG. 6B, in a conformal approach, fewer high throughput measurements resulted in a faster measurement time compared to current hyperspectral imaging (HSI) techniques. FIG. 6A shows a brightfield image and the resultant score image using current HSI techniques. FIG. 6B compares a discrete bandpass measurements plot, which contains more wavelength-measurements, compared to conformal measurements, which contain less wavelength-measurements. Both sets of data lead to the same results using partial least squares (PLS) and optical regression methods. Thus, a highly informative detection can occur when collecting fewer measurements, as in a conformal approach, than when using current HSI techniques and produce the same score image.

FIG. 7A shows a representative multivariate score image of a kidney that was generated through an applied classification algorithm based upon the results of a partial least squares discriminate analysis (PLS-DA) of spectra extracted from molecular images (full hyperspectral images) of excised kidneys. FIG. 7B shows a representative univariate score image of kidney that was obtained by division of two frames extracted at two wavelengths (FIG. 7B). FIG. 7C shows the Receiver Operator Characteristic (ROC) curve generated from each score image. Multivariate analysis yielded superior results as indicated by a higher area under the ROC (AUROC) of the multivariate score image when compared to that of the univariate score imaging. While univariate analysis may drastically reduce the time for data collection and analysis, sensitivity and specificity often suffer.

RtCE can be used to optimize a dual polarization conformal filter for high tissue type sensitivity and specificity by adjusting the voltage applied to the stages of the conformal filters based on image data obtained in real-time. In such embodiments, a measurement field of view (FOV) containing both tumor and non-tumor can be selected, and a reference image can be collected. The user can then define the tolerance for an intended tissue type and an associated figure of merit (FOM). The user defines an optical computation from a set of defined computations for the intended tissue type. The processor performs a non-linear optimization process and iterations of this process are performed until the FOM is minimized to the defined tolerance.

In some embodiments, the system may further include a non-transitory storage medium in operable communication with the processor. This storage medium may include various operating systems and other computer programs and hardware necessary to communicate with the controller and filters. In certain embodiments, the storage medium may include one or more programming instructions that, when executed, causes the processor to do the following:

(a) direct the controller to apply one or more voltages to the one or more stages of the first conformal filter to tune the first conformal filter to a first configuration;

(b) direct the controller to apply one or more voltages to the one or more stages of the second conformal filter to tune the second conformal filter to a second configuration;

(c) generate the one or more test data sets; and (d) analyze the one or more test data sets.

In some embodiments, the storage medium further contains one or more programming instructions that, when executed, cause the processor to select the first configuration from a LUT comprising one or more first tissue types, and select the second configuration from a LUT comprising the one or more second tissue types. In certain embodiments, the first configuration for filtering photons that have interacted one or more first tissue types may be used to identify a target tissue, and the second configuration for filtering photons that have interacted with one or more second tissue types may be used for identifying matrix, or non-target tissue types. In yet other embodiments, the storage medium may contain instructions that, when executed, cause the processor to apply one or more chemometric techniques to the image data. Of course, the storage medium may further contain any combination of the instructions described above.

Other embodiments are directed to methods for detecting or imaging the features of biological tissues using the devices and systems described above. In some embodiments, the methods may include the steps of separating photons that have interacted with biological tissues into a first optical component and a second optical component, passing the first optical component through a first conformal filter having one or more filter stages to generate a first filtered component; passing the second optical component through a second conformal filter having one or more filter stages to generate a second filtered component, individually applying voltages to each of the one or more stages of the first conformal filter and separately to each of the one or more stages of the second conformal filter; generating image data from the first and second filtered components; and generating an image of the biological tissue in which a first tissue type and a second tissue types are distinguished.

In some embodiments, applying voltages to each of the one or more filter stages of the first conformal filter and to each of the one or more stages of the second conformal filter configures the first conformal filter to conform to a spectral shape associated with the first tissue type and configures the second conformal filter to conform to a spectral shape associated with the second tissue type. In certain embodiments, applying the voltages, further comprises referencing a LUT comprising voltages associated with a first tissue type or a second tissue type that can be applied to each stage of the one or more stages of the first conformal filter and each stage of the one or more stages of the second conformal filter to identify the first tissue type or second tissue type. The voltages cause the conformal filter to which the voltages are applied to filter interacted photons that have interacted with a tissue component, such as a protein, sugar, DNA, RNA, or other biological molecule that is present in the target tissue but not present or present at lower concentrations or quantities in the matrix, non-target tissue. The tissue component may be an analyte. In such embodiments, by applying the voltages, the first conformal filter may be configured to filter a spectral shape associated with a first tissue component in the target tissue, and the second conformal filter may be configured to filter a spectral shape associated with a second tissue component in the matrix or non-target tissue. In various embodiments, the voltages may be applied actively, meaning that the voltages are applied and the filters are tuned in real time during image data collection.

In some embodiments, the first and second tissue components may be the same, and in other embodiments, the first and second tissue components may be different. In particular embodiments, image data associated with the first filtered component and the second filtered component may be collected by the same detector, and in other embodiments, image data associated with the first and second filtered components may be collected by different detectors. In certain embodiments, image data associated with the first and second filtered components may be collected by multiple detectors. The image data for the first and second filtered components can be collected simultaneously or sequentially, and in some embodiments, a method may allow for both simultaneous and sequential image data collection.

Embodiments are not limited to particular features that can be distinguished in the images created by the methods described above. For example, the features of the biological tissue may include, but are not limited to, anatomical features, normal tissue, abnormal tissue, tumors, tumor margins, large organ sections, surgical margins, and the like and combinations thereof.

Image data associated with the first and second tissue types may be acquired simultaneously. For example, in some embodiments, first image data may be acquired from the first conformal filter, and second image data may be acquired from the second conformal filter. The first image data and the second image data may be acquired or collected individually in sequential acquisition processes. In other embodiments, the first and second image data sets can be acquired simultaneously by separate detectors for each image data set or simultaneously by a single detector. In such embodiments, the first image data set may be image data relating to a target tissue or a tissue component in a target tissue, and the second image data set may be image data relating to non-target tissue or a tissue component associated with non-target tissue. In certain embodiments, the image data may include image data from any spectral band including the VIS, NIR, or SWIR, and the image data may include a VIS data set, a NIR data set, and a SWIR data set.

In particular embodiments, generating an image may include analyzing the image data. In such embodiments, analyzing may include applying one or more optical computations to the image data. In certain embodiments, the optical computation may include, for example, $T_1$, $T_1-T_2$, $(T_1-T_2)/(T_1+T_2)$, and combinations thereof, wherein $T_1$ is a first reflectance image and $T_2$ is a second reflectance image. In still other embodiments, analyzing may further include applying one or more chemometric techniques to the image data.

In various embodiments, the methods may further include directing the controller to apply a voltage to the one or more stages of the first conformal filter to tune the first conformal filter to a first configuration; and directing the controller to apply a voltage to the one or more stages of the second conformal filter to tune the second conformal filter to a second configuration. In still other embodiments, the methods may include selecting the first configuration from a LUT comprising the one or more tissue types, wherein the LUT comprises one or more voltages associated with the one or more stages of the first conformal filter to configure the first conformal filter to a first tissue type; and selecting the second configuration by consulting a LUT comprising the one or more tissue types, wherein the LUT comprises one or more voltages associated with the one or more stages of the second conformal filter to configure the second conformal filter to a second tissue type.

All of the methods of the various embodiments can be incorporated into the systems described above and may be incorporated into the computer readable instructions available to the processor. As such, the methods may be used to distinguish and image any biological tissue such as, for example, kidney tissue, heart tissue, breast tissue, ovarian tissue, lung tissue, liver tissue, bladder tissue, intestinal tissue, stomach tissue, cornea tissue, lens tissue, bone tissue, and skin tissue.

By exploiting these modalities, a device of the present disclosure holds potential for use by surgeons to provide diagnostic information in real time and without the use of reagents. With the employment of conformal filter technology and dual polarization, simultaneous data acquisition at two discrete wavelengths will result in faster data acquisition and higher throughput. This holds potential for providing an intraoperative, label-free cancer margin detector that is capable of generating diagnostic information in real time which combines the high sensitivity and specificity of multivariate techniques with the rapid acquisition time of univariate techniques.

While the invention has been described in detail in reference to specific embodiments thereof, it will be apparent to one skilled in the art that various changes and modifications can be made therein without departing from the spirit and scope of the embodiments. Additionally, while the examples provided herein related to specific tissue types, the present disclosure is not limited to these tissue types and may be used to detect a wide variety of tissue types of interest. Thus, it is intended that the present disclosure cover the modifications and variations of this disclosure provided they come within the scope this application.

EXAMPLES

Example 1

FIGS. 8 and 9 are illustrative of the detection capabilities of the intraoperative optical diagnostic devices and systems described above. The system used relies on a robust design algorithm in order to produce an appropriate optical transmission function(s) for the intended analytical response as opposed to tuning to discrete wavelengths. As a result of the large spectral bandpass of the conformal filter, its optical throughput, and thus the measured signal to noise ratio (SNR), is considerably higher than similar filters operated in a single wavelength mode. In addition, the conformal filter approach requires fewer measurements to achieve tissue type specificity resulting in a faster measurement time as compared to conventional HSI. Not only does the conformal approach provide better detection performance for the target tissue type (highest Area Under the ROC Curve over all methods), the detection is made faster and demonstrates excellent discrimination between "near neighbors," i.e., tissue types with similar spectral features.

A pig kidney with ureter attached is used to demonstrate technical feasibility of discriminating between different tissue types using the intraoperative optical diagnostic devices and systems described above. The ureter 801 was selected as the tissue type of interest, and the other anatomic features, such as normal renal parenchyma (NRP 802) and fat 803, were selected as matrix (i.e., background). The sample was analyzed using an experimental set up as illustrated in FIG. 1 in which a quartz tungsten halogen lamp was used as an illumination source, the filter was a MCF conformal filter, and the detector was a CCD camera. RtCE methodology was applied to the image data collected using the device described above. Two VIS/NIR reflectance images (FIG. 8A, B) were generated. The optical computation was applied, and a score image FIG. 8C was generated. As illustrated in the detection image (FIG. 8D), the ureter 804 was detected and distinguished from the majority of the background features.

FIG. 9 shows the statistical analysis of the score image reproduced as FIG. 9A. A probability distribution FIG. 9B, illustrates in-class v. out-of-class detections on a pixel-by-pixel basis. The ROC curve FIG. 9C was generated by applying a threshold to the probability distribution in FIG. 9B and illustrates the sensitivity and false positive results achieved. These results show that the intraoperative optical diagnostic devices and systems described above are capable of distinguishing between tissue types with excellent sensitivity and are capable of generating useful images showing tissue boundaries.

Example 2

FIG. 10 illustrates the enhanced contrast achieved by using intraoperative optical diagnostic devices incorporating dual polarization and conformal filters imaging a kidney and distinguishing between NRP, fat and ureter tissue. FIG. 10A shows a brightfield image of the entire kidney, ureter 1001, and surrounding fat 1003. The box indicates the region of interest from which the image data presented in FIGS. 10B-D were derived. FIG. 10B is an NIR reflectance image of the region of interest. FIG. 10C is an image acquired using the dual polarization confocal filter device configured as illustrated in FIG. 1. During data collection, one MCF confocal filter collected the image data at 965 nm, and the second MCF confocal filter collected an image data at 925 nm. The image in FIG. 10D was calculated by dividing the 965 nm image data by the 925 nm image data. Gaussian blurring of this image smoothed the image. FIG. 10D shows the improved contrast between the ureter 1001 and the NRP 1002 over the NIR and single frame dual polarization images in FIG. 10B and FIG. 10C. This improved contrast was created in a very short acquisition time comparable to a univariate system.

Example 3

FIG. 11 provides another example of the improved contrast provided by the intraoperative optical diagnostic devices incorporating dual polarization and conformal filters imaging a kidney. FIG. 11A is a NIR image of the region of interest. As illustrated in FIG. 11B and FIG. 11C, contrast between the ureter 1101 and the NRP 1102 is dramatically improved using the dual polarization conformal filter configuration described in FIG. 1. In this case, image data was collected through two MCF confocal filters at 740 nm and 930 nm. FIG. 11B is the resultant image after dividing the 740 nm image by the 930 nm image, and FIG. 11C is the divided image (FIG. 11B) after Gaussian blurring. These data again show the improved contrast of images acquired using the devices and systems described above over images acquired using current NIR devices.

What is claimed is:

1. A method for detecting one or more features of a biological tissue, the method comprising:

separating interacted photons comprising photons that have interacted with one or more analytes in a biological sample into a first optical path and a second optical path;

passing the first optical path through a first conformal filter comprising one or more filter stages and generating a first filtered component;

passing the second optical path through a second conformal filter comprising one or more filter stages and generating a second filtered component;

wherein the first conformal filter is configured to filter the first optical path and the second conformal filter is configured to filter the second optical path by:
referencing a Look Up Table (LUT) comprising one or more voltages associated with each stage of the one or more stages of the first conformal filter and each stage of the one or more stages of the second conformal filter;
applying one or more voltages to the one or more stages of the first conformal filter which configures the first conformal filter to conform to a spectral shape associated with a first analyte, and to the one or more stages of the second conformal filter which configures the second conformal filter to conform to a spectral shape associated with a second analyte;
detecting the first filtered component and the second filtered component and generating one or more test data sets; and
analyzing the one or more test data sets with a computer processor to detect the one or more features of the biological tissue by:
applying one or more optical computations to the one or more test data sets, wherein the one or more optical computations comprise at least one of a $T_1$, a $T_1-T_2$, or a $(T_1-T_2)/(T_1+T_2)$ computation, and
applying one or more chemometric techniques to the one or more test data sets.

2. The method of claim 1, wherein the one or more features of the biological tissue comprises one or more of an anatomical feature, a normal tissue, an abnormal tissue, a tumor, a tumor margin, a large organ section and a surgical margin.

3. The method of claim 1, wherein the first analyte and the second analyte are the same.

4. The method of claim 1, wherein the first analyte and the second analyte are different.

5. The method of claim 1, wherein the first filtered component and the second filtered component are detected by the same detector.

6. The method of claim 1, wherein the first filtered component and the second filtered component are detected by a plurality of detectors.

7. The method of claim 1, wherein the first filtered component and the second filtered component are detected simultaneously.

8. The method of claim 1, wherein the first filtered component and the second filtered component are detected sequentially.

9. The method of claim 1, wherein the one or more voltages are applied to the one or more stages of the first conformal filter and to the one or more stages of the second conformal filter actively.

10. The method of claim 1, wherein the one or more test data sets comprise a first test data set generated from the first conformal filter and a second test data set generated from the second conformal filter.

11. The method of claim 1, wherein the first data set represents one or more target analytes of the one or more analytes and the second data set represents a matrix comprising one or more non-target analytes of the one or more analytes.

12. The method claim 1, wherein the biological sample comprises one or more of kidney tissue, heart tissue, breast tissue, ovarian tissue, lung tissue, liver tissue, bladder tissue, intestinal tissue, stomach tissue, cornea tissue, lens tissue, bone tissue, and skin tissue.

13. The method claim 1, wherein the one or more test data sets comprise one or more of a VIS data set, a NIR data set, and a SWIR data set.

14. The method of claim 1, further comprising:
directing a controller to apply the one or more voltages to the one or more stages of the first conformal filter to tune the first conformal filter to a first configuration; and
directing a controller to apply the one or more voltages to the one or more stages of the second conformal filter to tune the second conformal filter to a second configuration.

15. The method of claim 14, further comprising:
selecting the first configuration from a LUT comprising the one or more analytes, wherein the LUT comprises one or more voltages associated with the one or more stages of the first conformal filter to configure the first conformal filter to a first analyte; and
selecting the second configuration by consulting a LUT comprising the one or more analytes, wherein the LUT comprises one or more voltages associated with the one or more stages of the second conformal filter to configure the second conformal filter to a second analyte.

16. The method of claim 15, wherein the first configuration comprises a configuration for detecting one or more target analytes from the one or more analytes and the second configuration comprises a configuration for detecting a matrix comprising one or more non-target analytes from the one or more analytes.

* * * * *